(12) United States Patent
Porumbescu (10) Patent No.: US 6,368,272 B1
(45) Date of Patent: Apr. 9, 2002

(54) EQUIPMENT AND METHOD FOR CONTEMPORANEOUS DECISION SUPPORTING METABOLIC CONTROL

(75) Inventor: Aureliu M. Porumbescu, Gainesville, FL (US)

(73) Assignee: Proactive Metabolics Company, Gainesville, FL (US)

( * ) Notice: Subject to any disclaimer, the term of this patent is extended or adjusted under 35 U.S.C. 154(b) by 0 days.

(21) Appl. No.: 09/290,094

(22) Filed: Apr. 12, 1999

Related U.S. Application Data (60) Provisional application No. 60/081,290, filed on Apr. 10, 1998.

(51) Int. Cl.⁷ .................................................. A61B 5/00
(52) U.S. Cl. ....................... 600/300; 600/361; 128/898
(58) Field of Search ................................ 600/300–301, 600/309, 361–365, 345; 128/898, 920–925; 434/265

(56) References Cited

U.S. PATENT DOCUMENTS

| | | | |
|---|---|---|---|
| 4,055,175 A | 10/1977 | Clemens | |
| 4,151,845 A | 5/1979 | Clemens | |
| 4,206,755 A | 6/1980 | Klein | |
| 4,245,634 A | 1/1981 | Albisser | |
| 4,475,901 A | 10/1984 | Kraegen | |
| 4,559,037 A | 12/1985 | Franetzki | |
| 4,731,726 A | 3/1988 | Allen, III | |
| 4,822,337 A | 4/1989 | Newhouse | |
| 4,871,351 A | 10/1989 | Feingold | |
| 5,019,974 A | 5/1991 | Beckers | |
| 5,216,597 A | 6/1993 | Beckers | |
| 5,251,126 A | 10/1993 | Kahn | |
| 5,364,346 A | 11/1994 | Schrezenmeir | |
| 5,462,051 A | 10/1995 | Oka | |
| 5,497,772 A | 3/1996 | Schulman | |
| 5,542,420 A | 8/1996 | Goldman | |
| 5,665,065 A | 9/1997 | Colman | |
| 5,822,715 A | 10/1998 | Worthington | |
| 5,840,020 A | * 11/1998 | Heinonen | |
| 5,868,669 A | 2/1999 | Iliff | |

OTHER PUBLICATIONS

Porumbescu, A., et al., Proceedings of the Fourth International Federation of Automatic Control/System Structure and Control [Oct. 1997], pp. 396–401.

* cited by examiner

Primary Examiner—Robert L. Nasser
Assistant Examiner—Michael C Astorino
(74) Attorney, Agent, or Firm—Saliwanchik, Lloyd & Saliwanchik (57) ABSTRACT

The invention addresses hardware and software products capable to make contemporaneous accurate predictions regarding how a person's biological system will respond to a series of stimuli. The predictions can then be communicated in real time, enabling confirmation of good control status, need for corrective action, planning future actions, or even outside intervention in case of emergency. Also addresses by the invention is a family of diagnostic hardware based on intelligent optoelectronic sensors that incorporate one or more Wedge-and-Strip Position-Sensitive Photo-Detectors optimized for probabilistic real time evaluation of spectroscopy data from living subjects.

19 Claims, 4 Drawing Sheets

EQUIPMENT AND METHOD FOR CONTEMPORANEOUS DECISION SUPPORTING METABOLIC CONTROL

CROSS-REFERENCE TO RELATED APPLICATION

This application claims the benefit of U.S. Provisional Application No. 60/081,290 filed Apr. 10, 1998, hereby incorporated by reference in its entirety.

The invention described herein was made in the performance of work under National Institutes of Health (Contract Number LR43 DR47730-01A2) and Department of Defense (Contract Number DASG60-97-M-0066) contracts. The federal government may have certain rights in this invention.

BACKGROUND OF THE INVENTION

In health, all events taking place inside living bodies are controlled by a myriad of minute processes, each having outcomes preordained by their DNA templates. One such process is the blood glucose metabolism, which is optimized to achieve normoglycemia even for wide swings in the predominant effect inputs, food and physical exercise. Illness, on the other hand, is characterized by the body's inability to maintain control over one or more biological processes. Unless correctable by surgery, medication, or other means, the out-of-control condition extends to other processes and results in poor patient prognosis. The only alternative left to people suffering from "incurable" afflictions is disease management, that is, careful monitoring of the parameters of interest, coupled with corrective actions such as insulin injections, dialysis, etc.

For example, diabetes patients have little or no endogenous blood glucose (BG) control capability, and many must inject insulin to compensate for swings outside the acceptable serum glucose range. Similarly, end-stage renal disease patients have lost the ability to control their nitrogen metabolism, and must undergo dialysis, typically for the rest of their lives. The reader will appreciate that many other situations sadly exist, however, because they are representative of this entire class of problems, we will limit the examples presented here to glucose control and diabetes, and their spin-off, long-term weight management.

Diabetes mellitus is a significant chronic disease with no cure, affecting more than 16 million Americans and 100 to 150 million people worldwide. In the U.S. it is the fourth-leading cause of death each year. (National Institutes of Health/National Institute of Diabetes and Digestive and Kidney Diseases: Diabetes in America/Second Edition, NIH Publication No. 95-1468 (1995)). Its incidence rate among children and teenagers in the U.S. increased several fold during the last thirty years, and more than 30,000 new cases are identified each year. It is a $156 billion problem for the US economy.

A problem of this magnitude naturally generates intense efforts to alleviate it, and one landmark study has altered the course of treatment. The results of the Diabetes Control and Complications Trial (DCCT) indicate that tight control of blood glucose levels results in a dramatic reduction of complications, including 76% lower incidence of diabetic retinopathy, 60% less neuropathy, and as much as 56% fewer cases of nephropathy. The costs to society could be drastically reduced, but at the expense of intensive management (more frequent blood sugar measurements, multiple daily injections).

Technological advances have made it possible for patients to administer insulin at home, and to monitor the blood glucose levels (self monitoring of blood glucose, or SMBG) with equipment that costs less than $100; test strips and accessories run about $2,000 per year per patient, but of course this expense will double with intensive management as suggested by the DCCT results. To further improve ease of control, intense product development efforts have led to the introduction of a new, rapid insulin (HUMALOG™), and non-invasive blood glucose measurement equipment could be marketed within the next few years.

However, currently available equipment does not take into account the blood glucose dynamics, and invasive blood glucose measurement techniques discourage frequent testing. The blood glucose values are therefore known only to a minute extent, because even the most compliant patients will only draw blood and test the glucose concentration less than ten times a day. The data available is therefore much too far from the Nyquist sampling rate, and very little information results from the individual blood tests. Again, intense product development efforts have led to the introduction of statistical process control concepts in blood glucose meters, and many now can store several hundred measurements, including the time of day and date each value was measured. For a rigid regimen, whereby the patient always eats the same meals at the same time, and injects the same amounts and types of insulin every day at the same time, the statistical information thus gathered helps with the metabolic control and gives the physician the means to assess the patient compliance and adequacy of the regimen. The main drawback of this methodology is that it is all after the fact, while also severely restricting the patients' freedom of action in the most basic areas, such as food and exercise, and rest.

This too has a solution, albeit an imperfect one: the "gold standard" in diabetes nutrition is carbohydrate counting, a method that allows the patients with insulin-dependent diabetes to eat any higher carbohydrate meal, so long as the equivalent amount of insulin is administered. There are problems with this also, the two most important being that most patients cannot do the conversion, and that not all carbohydrates are equal in terms of their speed of conversion to blood glucose. (An extensive amount of information exists on the glycemic index of different types of food.)

Intense efforts to introduce non-invasive blood glucose testers will soon bring to market equipment that will make frequent testing convenient, but still no predictive capability will be added by non-invasive SMBG. The burden of understanding the temporal characteristics of the physiological mechanisms of glucose regulation depends on the patients.

Those equipped with the knowledge and willingness to devote time are able to achieve a good overall level of control, but most patients are overwhelmed and find themselves unable to understand what has caused the lack of blood glucose control. For patients who are not equipped with the ability to understand such issues, the only way to stay in control is to adhere to a very stringent schedule of daily insulin, food and exercise that does not vary from one day to another. Such a regimen poses serious compliance and lifestyle problems. For these patients, solutions based on mathematical modeling are available:

The body of a healthy person has the endogenous control capability to minimize the glycemic challenge to the body, but the diabetes patient has little or no endogenous control capability. Maintaining blood glucose levels within normal limits can be treated as a control systems engineering problem, which was, and continues to be the object of much research. Those who published their work in this field (Heinonen, Porumbescu, etc.) considered the body's blood glucose system a classic control system, consisting of a plant whose aim is to maintain control over an output (Blood Glucose), in the presence of zero or non-zero inputs (food, physical exercise, insulin), and of perturbations (emotional status, illness). The euglycemic output is achieved by feedback: continuously measuring the output values, comparing them to the desired state (set point), and initiating compensatory action. By contrast, in diabetes this is an open-loop system, in need of an external feedback loop, therefore attempts were made to provide it through mechanical means.

After more than twenty years of trying, it can be safely said that attempts to devise mathematical models for blood glucose metabolism have failed. The reasons are numerous, but one of the most important is that models that will work properly for an entire population are very complicated and include nonlinear equations. Some degree of success has been reported with developing adaptive individual-specific models, which will work in conjunction with a strict regimen that does not vary from one day to another.

Figure 1:
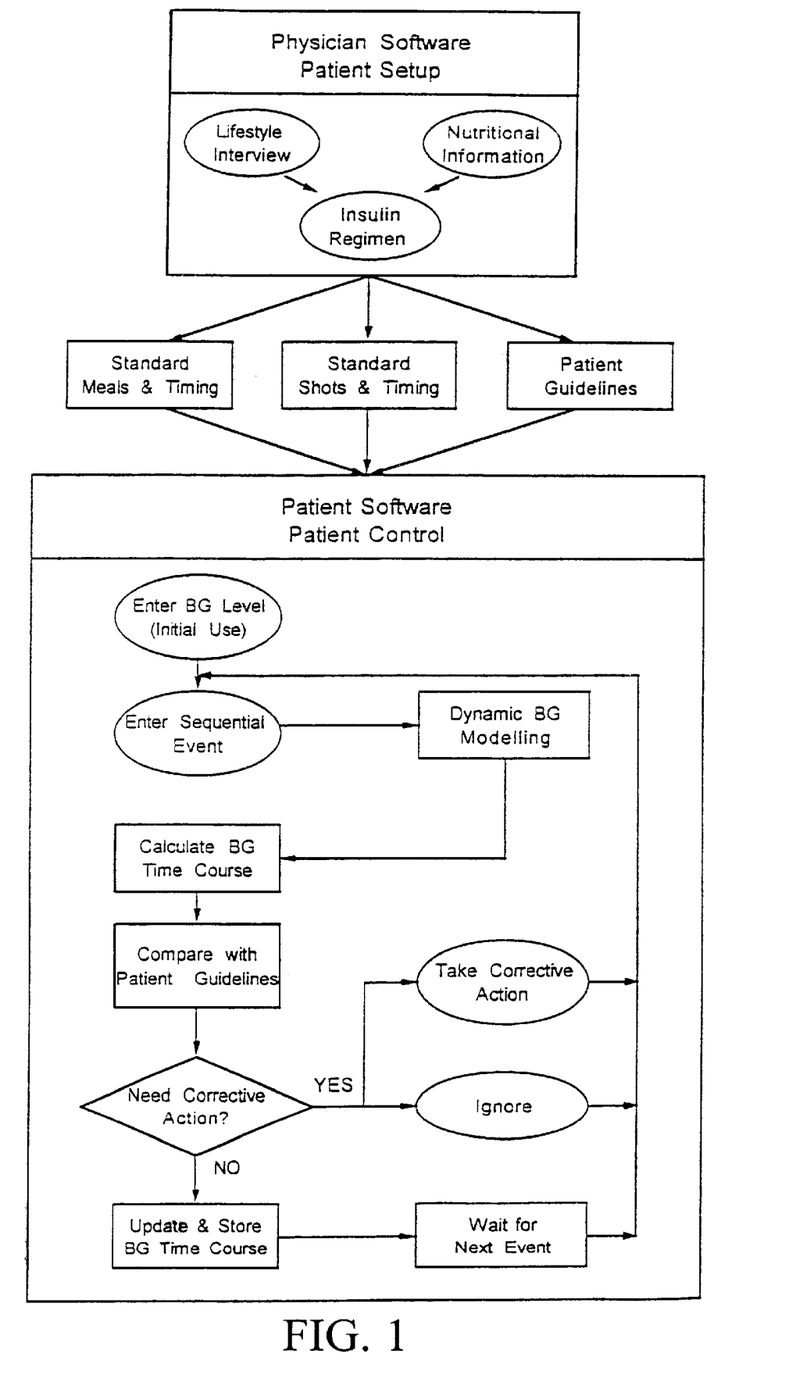
FIG. 1: A flow chart and block diagram of the software and steps involved.
Figure 2:
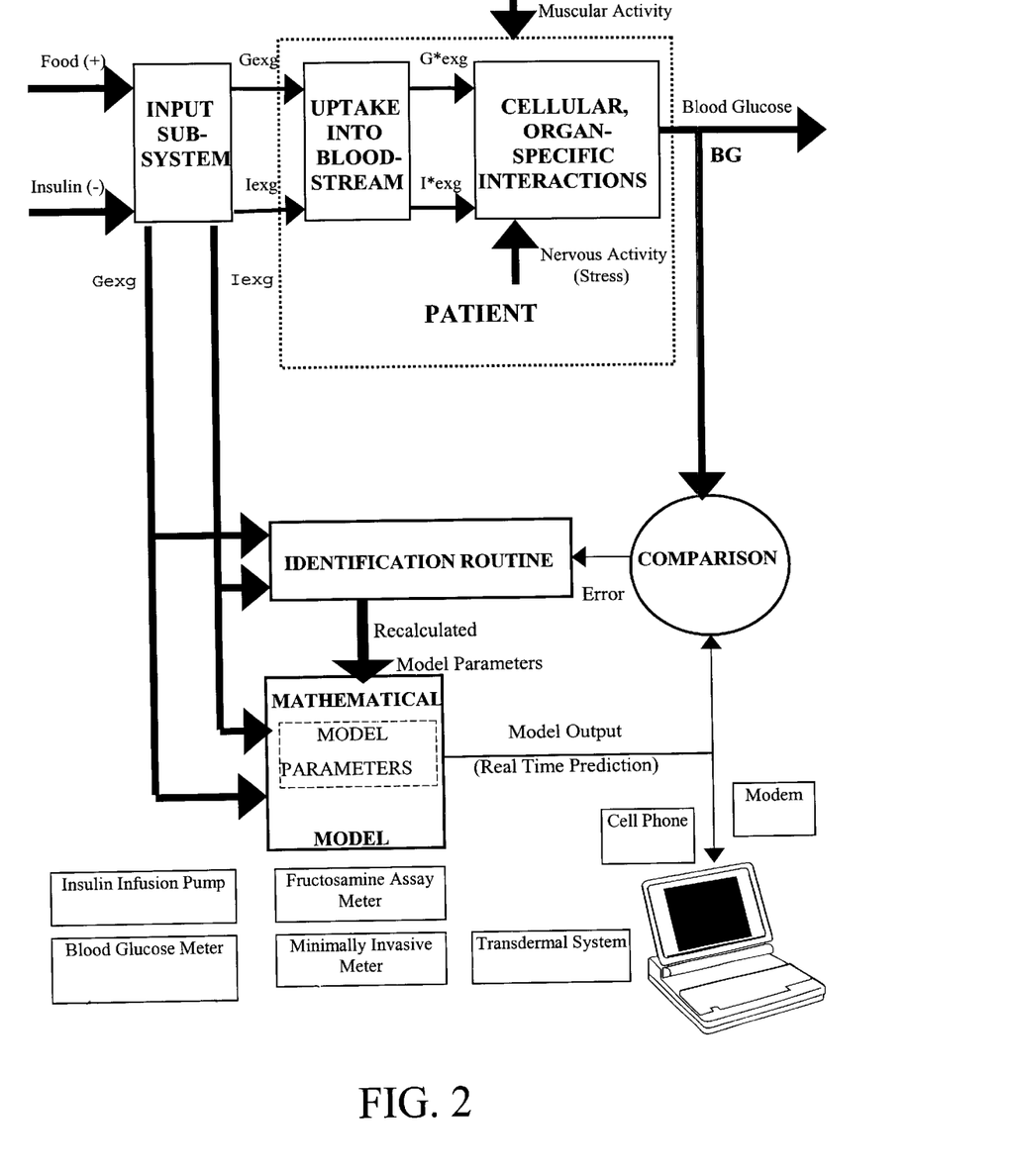
FIG. 2: Diagram showing the system, including software, hardware, and patient.
Figure 3:
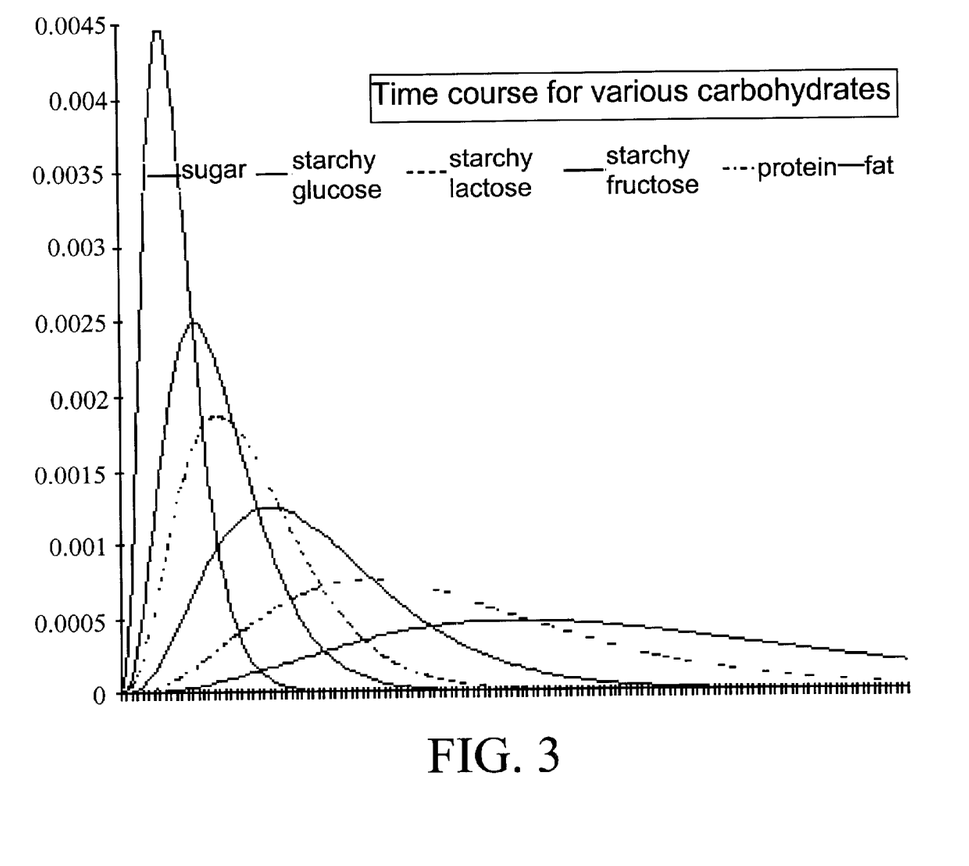
FIG. 3: Graph illustrating the differences in glucose bio-availability for different types of food, computed according to the invention.
Figure 4:
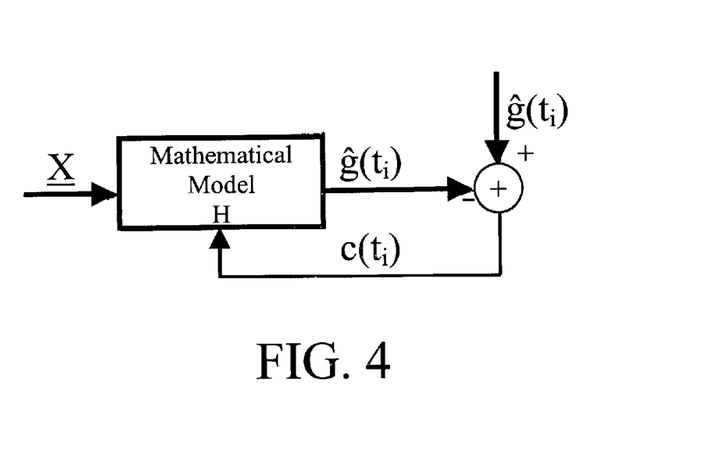
FIG. 4: Prior art illustration of "static" adaptive model.
Figure 5:
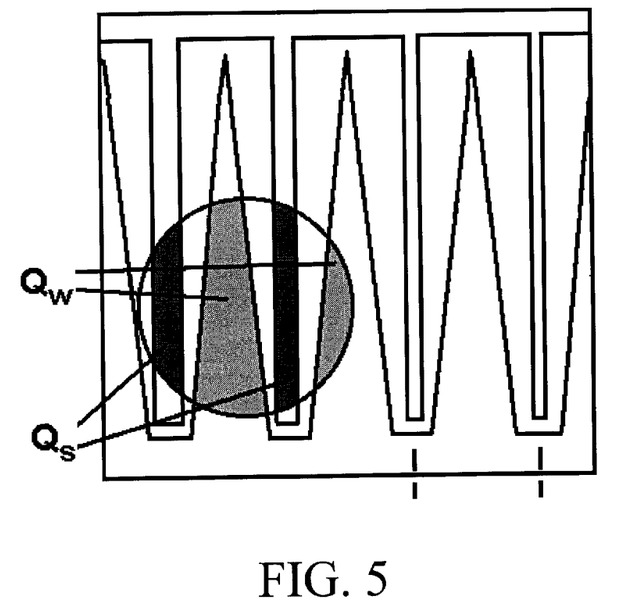
Figure 6:
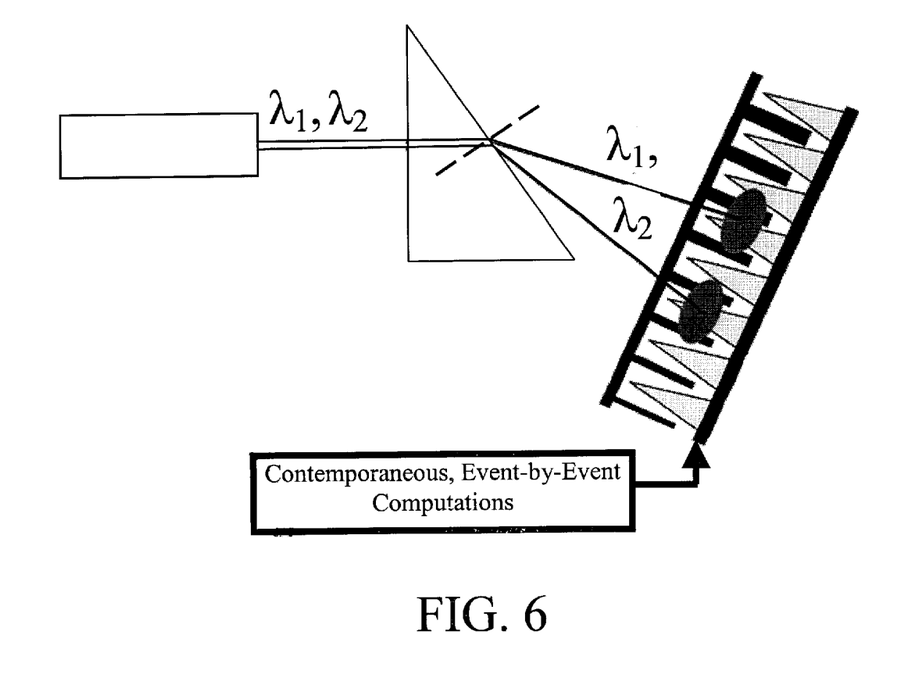
FIG. 6: Optical Spectroscopy apparatus having a wedge-and-strip array as photodetector.

For example, U.S. Pat. No. 5,840,020 (Heinonen et al.) addresses the adaptive model shown in FIG. 4, whereby the error between a predicted value and the actually measured value is used to optimize (converge) a dynamical model in a recursive fashion, using Widrow's Adaptive Least Means Square algorithm.

Similarly, Porumbescu et al. ("Patient Specific Expert System For IDDM Control" in Proceedings of the Fourth Conference of the International Federation of Automatic Control/System Structure and Control, October 1997) report on the development of an Expert Equipment that optimizes a dynamical model using Kalman recursive filtering.

The rapid spread of increasingly affordable high speed computers gives this type of research more impetus, and several researchers have recently reported significant progress. One commercial software package, based on a very simple prediction model has been introduced in 1995 (Insulin Therapy Analysis, by ITA Software Inc.). The AIDA Interactive Diabetes Advisor, which uses a similar modeling and prediction approach is available over the internet. Yet another system, KADIS, is in use in Germany as a model-aided education tool for IDDM patients.

What all these solutions have in common is the inability to process the information and generate predictions in an on-going manner. For this reason they are more in the nature of educational tools, than of assistive devices. While they may, to some extent, be able to generate sufficiently accurate predictions, those predictions apply only to a known and very rigid, set of inputs. And, while with a good model, the patient will likely be able to generate a close enough prediction for one different input one time, the performance cannot generally be repeated several times in a row, because the initial conditions have changed.

The complicating factor is that to achieve contemporaneous control, the modeled external feedback loop must include not only static corrections, but also predictive elements relative to the dynamics of the patient's body.

BRIEF SUMMARY

The present invention relates to decision support equipment and improved methods for providing individuals with means to proactively control their health. The invention subject also relates to computing equipment suitable for processing data to simulate the dynamics of the metabolic processes and their inputs, in order to generate real time predictions of the metabolic status. The subject invention further relates to knowledge-based apparata used in controlling management-intensive medical conditions, including apparata for noninvasive assays of metabolic analytes.

BRIEF DESCRIPTION OF DRAWINGS

FIG. 5: Principle of operation of the wedge-and-Strip position-sensitive detector (prior art): The centroid position computation in Wedge-and-Strip patterns is based on the following property of the wedge-and-strip inter-digital pattern: An electron cloud, having diameter larger than the pitch, lands on the pattern. With the collected charges $Q_s$, $Q_w$ as shown, and $Q_0$ for the substrate, the [X,Y] coordinates of the centroid of the cloud are simply computed as:

$$X=2 \cdot Q_s/(Q_s+Q_w+Q_0)$$

$$Y=2 \cdot Q_w/(Q_s+Q_w+Q_0)$$

DETAILED DISCLOSURE

Decreasing costs for computers and communications and increasing pressures to contain health care costs promote technology-intensive proactive approaches to health care, especially in diabetes, but the invention is also applicable to any other medical condition where measurements are routinely made. The main benefit is that the patient has the ability to implement proactive actions that do not affect his or her life style in a major way, which leads to greatly improved health outcomes and compliance.

The invention puts control ahead of measurement, giving people the means to understand what is happening with their bodies with respect to a set of parameters of interest, relying on the fact that proactive control is more desirable than the current test-fix-test (an approach with which one is instinctively comfortable). To that end, the invention provides a group of software programs and ancillary equipment to compute an individual patient's profile and make contemporaneous accurate predictions regarding how the patient's biological system will respond to individual stimuli: predictions are communicated in real time, enabling plans for future actions by verification of good control status, or signaling the need for corrective action. Thus, contemporaneous decision support is provided to the patient.

The subject invention provides for customizing traditional population-based solutions to an individual patient's needs and adding the time dimension (i.e., attaching a time function to each variable of interest). This approach is superior because it allows prevention-driven proactive care at the health care consumer level, when the consumer needs the information, not after the fact. It is also more accurate and effective:

The invention is based on three basic concepts: 1) Control is more relevant than measurement. Devices of the future, which will mimic life itself, must target the overall success of metabolic control—keeping the parameters of interest within the target range—to know any value with accuracy and precision is less relevant. A patient-specific system model converges much quicker to "good enough" approximations of the outputs of the real system than one that only uses general population data; 2) Proactive control mimics life. In control systems parlance, these are "feedforward" systems as opposed to measure-and-correct, or "feedback" that we accept instinctively. Unlike current devices that test something and generate a value that must be processed to generate information, our noninvasive measurement devices aim to use the prior knowledge about the dynamics of the system being measured, in order to generate "heads up, in or out of control" signals, usable directly by the consumer; and 3) Living things reflect the dynamics of their inputs—this is borne by research in system control theory, which indicates that stable feedforward systems have structures that are actually governed by the dynamics of their input functions.

Ultimately, these basic concepts mean that the invention addresses the problem from a duality point of view: Dualities between control and estimation problems are useful concepts in optimal control theory because by demonstrating a duality, the solution to one set of problems can be applied also to the dual set of problems. As discussed by Bernhardsson et al. "A duality is demonstrated between optimal feedforward control and optimal deconvolution, or input estimation. These two problems are normally discussed separately in the literature, but have close similarities." Managing a management-intensive disease such as diabetes involves an individual about whom considerable knowledge exists, and knowing when to test is usually more important than the test results. With careful consideration of all major inputs and outputs, total system models can predict much of what is occurring; therefore total system individual-specific modeling is as important as the measurement method, be it invasive or noninvasive.

Blood glucose and interstitial fluid glucose dynamics are dominated by smooth time functions that describe the temporal transformation of a food input to glucose (the output): To that end, using carbohydrate counting to simulate the system input in conjunction with a feedback model, no matter how accurately the carbohydrates are counted, is like hitting a radio with a hammer and calculating its Dirac pulse response in order to understand how it's built.

The methodology to describe the exogenous glucose dynamics for various foods which is part of this invention is the direct result of this challenge. Rather than aiming for measurement accuracy and precision, the objective of the invention is to provide the individual with sufficient information to achieve proactive metabolic control, including the optimal timing and specifics of key activities such as insulin injections, blood glucose measurements, meals, exercise, etc. That is, to pursue regimen flexibility instead of rigidity. Using the models for the input dynamics results in a drastic simplification of the complexity of the models of the metabolic system.

Progress in the area of non-invasive SMBG will complement the methodology by providing more frequent clinical data points and thus helping the model converge to a sufficient prediction accuracy within a shorter time period. For IDDM patients who will not be able to afford the non-invasive SMBG equipment, the use of predictive technology in conjunction with a HUMALOG™ (lispro) type of insulin will be able to achieve euglycemia.

The subject invention provides methods of generating ongoing status predictions for improved decision support in metabolic control, comprising at least one of the following steps:

(a) entering ongoing information from the user-patient and from biomedical assay equipment according to an interactive, time-stamped mode which includes at least one of the following sub-steps:
  (a)(1) selecting and specifying inputs to the living system being controlled, plus specific descriptors and quantifiers of said inputs, wherein the said inputs may include nutrients, medication, physical activity, illness, or hormonal challenges;
  (a)(2) recording individual-specific anthropometrical, medication prescriptions, and treatment regimen data, wherein the said treatment regimen data also includes physician-prescribed metabolic control guidelines, including rules that define the "in-control range" and "sufficiently close" terms;
  (a)(3) selecting output parameters and entering their measured values; and
  (a)(4) selecting hypothetical inputs, wherein the user can evaluate a course of action over other possible actions.
(b) accepting or rejecting said input and output values and storing the information contained therein in appropriate memory areas, wherein each associated time stamp is properly stored as well;
(c) assigning to each said specified input an appropriate time function describing its dynamic characteristics and computing the predicted values thereof in an ongoing manner, starting said predictions from the time of the appropriate time stamp data;
(d) assigning to each said output parameter a mathematical model describing its dynamic interactions with the said inputs and improving said mathematical model by making it individual-specific by the following sub-steps:
  (d)(1) accepting individual-specific anthropometrical data and storing the information contained therein in appropriate memory areas;
  (d)(2) performing appropriate computations, wherein said anthropometrical data is incorporated in each said output parameter mathematical model;
(e) generating ongoing metabolic status predictions by combining all previous relevant said inputs with said individual-specific mathematical models, wherein the accuracy of the said predictions is improved by one or more of the following sub-steps:
  (e)(1) selecting from the universe of possible mathematical models only those that meet physiologically meaningful periodicity criteria, wherein they reflect circadian, menstrual and other applicable cycles that affect the process; and
  (e)(2) further improving the said mathematical models by selecting from the universe of possible mathematical models only those that lead to predicted values that are "sufficiently close" to the actual measured values.
(f) recording, revising and storing the prescribed individual-specific medication and control parameter limits, wherein a health practitioner sets boundaries on the type of actions the patient can take; and
(g) communicating to the patient the need for proactive corrective action, wherein any such need is determined by considering steps (e) and (f).

The subject invention also provides methods for estimating the ongoing "dynamic bio-availability" of metabolites subject to control, comprising at least one of the following steps:

(a) dividing the intake matter into distinct components, whereas each component is uniquely characterized by the dynamics of its transformation into a metabolite;

(b) assigning each said distinct component to an elementary category, wherein each category is described mathematically by a category-specific time function;

(c) calculating the time functions corresponding to the said distinct components, by accounting for all relevant quantifiers available for the intake matter; and (d) calculating the combined effect of said elementary components as a function of time.

The intake matter may be food, and the metabolites are "exogenous glucose" from food. Category-specific time functions are described by a time function having a general form such as would be required to describe mathematically the output from a chain of N compartments connected with one-way fluxes of the same rate a, given for example by, but not limited to, the expression:

$$EG(t)=a^N t^{N-1} e^{-at}/(N-1)$$

wherein "EG(t)" is elementary food component glucose activity time function; "t" is a length of time measured from the time stamp of entered data, such as the time the food was consumed; "a" is the flux rate of elementary food categories; and "N" is the number of compartments. In various embodiments, "a" is a population average value, "a" is specific for a given individual, or a=12 for all sugars, a=1/1.5 for starchy glucose, a=1/2 for starchy galactose, a=1/3 for starchy fructose, a=1/5 for protein, and a=1/8 for fats, and N=1 to 5, Some embodiments provide for N=4.

Elementary food categories are simple sugars, starches, protein, and fat, wherein each of the said elementary categories is described by a unique pair of coefficients a and N. The elementary food categories are further refined by executing at least one of the following steps:

(a) dividing each food category into sub-categories, each said sub-category being described by its unique pair of coefficients a and N;

(b) dividing the food category "starches" into three sub-categories corresponding to glucose-based, galactose-based, and fructose-based carbohydrates; and (c) adjusting the values of any said pair of coefficients a and N to reflect any individual-specific differences in ability to process the said category or sub-category of food.

Contemporaneous decision support in metabolic control may be achieved for diabetes, by pursuing two or more of the following steps:

(a) generating time functions describing the time course of the exogenous glucose following a meal, according to the methods provided herein;

(b) generating time functions describing the time course of the exogenous insulin following an injection or infusion pump action, according to the following method:

(b)(1) generating specific time functions having a general form such as would be required to describe mathematically the output from a chain of N compartments connected with one-way fluxes of the same rate b, given for example by, but not limited to, the expression:

$$1(t)=b^N t^{N-1} e^{-bt}/(N-1)$$

wherein b takes specific values for each different insulin formulation;

wherein "I(t)" is an exogenous insulin time function; "t" is a length of time measured from the time stump of entered data, such as the time the particular insulin was injected; "a" is the flux rate of various insulin types; and "N" is the number of compartments. In various embodiments, "b" is a population averaged value, "b" is specific for a given individual, or b=1.0 for regular insulin, b=0.5 for NPH insulin, b=0.25 for lente insulin, and b=0.2 for ultralente insulin. N can be a value from 1 to 5. Some embodiments provide for N=4.

(b)(2) refining said exogenous insulin time functions by accounting for the differences in insulin bio-availability experienced by the patient depending on the injection site; and (b)(3) refining said exogenous insulin time functions by accounting for the differences in insulin bio-availability experienced by the patient depending on the patient's degree of insulin resistance.

(c) generating time functions describing the time course of the physical exercise and other manually-entered inputs, according to the following method:

(c)(1) generating specific time functions having a general form such as would be required to describe mathematically the output from a chain of N compartments connected with one-way fluxes of the same rate c, given for example by, but not limited to, the expression:

$$PE(t)=c^N t^{N-1} e^{-c(t-d)}/(N-1)!$$

wherein c takes specific values for each different type of exercise, and d is a delay factor; and (c)(2) refining said physical exercise time functions by accounting for the differences in insulin bio-availability experienced by the patient depending on the injection site; and (c)(3) accounting for the additive or subtractive effect of illness, medication, or hormonal challenges by correcting the insulin input information accordingly.

The subject invention also provides a personal assistive apparatus for contemporaneous metabolic control, wherein a health practitioner programs the prescription and limits the type and extent of actions a patient is allowed to take by means of a hierarchical software structure. The invention also provides an apparatus for computing the bioavailability of exogenous glucose and other nutrients contained in food, consisting of:

(a) an interface and control device that accepts user input and provides information for the assessment and control of the ongoing metabolic state of the individual user;

(b) a data storage device containing an addressable food data base, and software wherein each element in the said food data base is decomposed vectorially into elementary food categories;

(c) a data storage device that contains a plurality of coefficient values and time function formats, wherein such coefficients and time functions appropriately describe the expected variation in time of one or more metabolites in vivo, under certain input conditions; and (d) software and means for computing and storing the predicted input time functions for the characteristics of the specified inputs.

The personal assistive apparatus for contemporaneous metabolic control may further comprise a means for determining the current values for at least one output parameter, such as the blood glucose level, wherein such determination results from direct input by the individual patient, or from direct download from an instrument measuring the concentration of said blood glucose; software and means for computing the estimated current values for the said blood glucose level; software and means for comparing the estimated current values for the said blood glucose level with their contemporaneous measured correspondent values, in order to optimize the mathematical model of the metabolic control system; software and means for predicting values for the future state of the blood glucose level, including means to decide if and when said blood glucose values are expected to fall outside the range defined by the "in-control" rules; and/or a means for alerting the user whenever any such predicted output parameter values fall outside the range defined by the "in-control" rules. The device may also present information to the user, through a graphical user interface, a color-coded or pictorial representation of the time course of the blood glucose, enabling the user to assess how every new action taken will modify the said representation.

The personal assistive apparatus for contemporaneous metabolic control may further comprise a means to compute and store functions indicative of the degree of control achieved by the individual patient over a period of time, such functions consisting typically of the aggregation of the severity-weighted time integrals of all out-of-control situations likely to have been experienced by the patient over the reporting period. Additionally, the personal assistive apparatus for contemporaneous metabolic control can further comprise at least one of the following devices: an insulin infusion pump; a blood glucose meter; a modem for communicating with other computers; wireless communication means for emergency situations; a meter that can test both glucose and fructosamine in the blood; a non-invasive blood glucose meter; a minimally-invasive blood glucose meter; a transdermal glucose measurement system. Alternatively, the personal assistive apparatus for contemporaneous metabolic control may further comprise an intelligent sensor consisting of at least: an optical spectroscopy apparatus employing at least one Wedge-and-Strip Position-Sensitive Photo-Detector, including means to detect the location of light pulses by employing analog decoding means; a means to illuminate a portion of a patient's body and onward the said Wedge-and-Strip Position-Sensitive Photo-Detector with light in certain portions of the infrared spectrum, wherein such illumination may be applied in a pulsatory fashion; a means to synchronize such light pulses with certain biological events, such as the heart beats; a means to accumulate the pulses read by the Wedge-and-Strip Position-Sensitive Photo-Detector into a histogram; means to calibrate the said optical spectroscopy apparatus by correlating the number of counts per second recorded in a certain portion of the histogram with the glucose concentration; a means to modify the duration of the measurement; and/or software for adapting the duration of the measurement according to the degree of prior knowledge about the analyte.

The personal assistive apparatus for contemporaneous metabolic control can further comprise software for optimizing the peritoneal dialysis prescription of patients with diabetes who suffer from kidney disease or for optimizing the metabolic control regimen of pancreatic or protected beta-cells transplantation patients. The software can be optimized for the metabolic control regimen of newly diagnosed diabetes patients in a hospital or clinic setting. Alternatively, the software for optimizing the metabolic control regimen of astronauts during space flights or for optimizing the metabolic control regimen of people with special glucose metabolism needs, including but not limited to patients under intensive care, patients who have suffered trauma, premature babies, or people involved in performance sports.

Definitions

The term "acceptable serum glucose range" is intended to mean glucose levels above 50 mg/dl and below 300 mg/dl more preferably 80 mg/dl to 200 mg/dl and most preferably about 100 mg/dl. It will be understood by those skilled in the art that levels of about 50 mg/dl are considered low and that levels of about 300 mg/dl are considered high, although acceptable in the sense that these levels are generally not fatal.

Insulin Dependent Diabetes Mellitus, or IDDM is a syndrome of disordered metabolism, leading to hyperglycemia due to an absolute deficiency of insulin secretion. The only known way to prevent the patient's death is by administering insulin.

The term "metabolism" is used here in its general sense, and it summarizes the activities each living cell carries on.

The term "dynamic bio-availability" reflects the time course of a certain metabolite, typically expressed as the changes in its quantity in blood.

The term "exogenous blood glucose" means glucose appearing in the blood stream as a result of the steps involved in assimilating food.

The term "in-control range" is a patient-specific term, reflecting the physician's assessment of the range of values within which a patient must try to maintain the metabolite being controlled.

Insulin Dependent Diabetes Mellitus, or IDDM is a syndrome of disordered metabolism, leading to hyperglycemia due to an absolute deficiency of insulin secretion. The only known way to prevent the patient's death is by administering insulin.

Normoglycemia is a patient-specific state, which can be thought of as a metabolic set point of 100 mg/dl, within a "normal range of 60 to 120 mg/dl. The specificity means that, for example, a person's blood glucose may never exceed 120 mg/dl, while another's may exceed 150 after every meal due to that person's increased resistance to the counter-regulatory hormone insulin, or it may go below 50 mg/dl every day, due to some prolonged physical strain at work, or due to over-excretion of insulin.

The term "sufficiently close" is used here in the following sense: a confidence band of physiologically-significant width around the measured metabolite values, that must contain all the predicted values for that metabolite for the same time stamp and input history combinations.

The term "time-stamped", as used in conjunction with information events entered into the device, means associating each such event with the correct time it has occurred, either through mechanical means or by having the user actually enter the correct time into the device. While there have been described what are believed to be the preferred software and hardware embodiments of the invention, those skilled in the art will recognize that other and further modifications may be hereto without departing from the spirit of the invention, and it is intended to claim all such embodiments fall within the true scope of the invention.

I claim:

1. A method to generate ongoing metabolic state predictions for improved decision support in metabolic control, comprising the following steps:

(a) entering into an apparatus ongoing metabolite contemporaneous time-stamped inputs from a user-patient and from biomedical assay equipment according to an interactive, time-stamped mode;

(b) allowing said user-patient to accept or reject the contemporaneous time-stamped inputs and storing the accepted inputs in appropriate memory areas of said apparatus;

(c) selecting one or more biological analytes (metabolite output values) to be controlled proactively using metabolic state predictions;

(d) assigning to each said metabolite contemporaneous time-stamped input an appropriate time function that describes its dynamic characteristics;

(e) computing predicted values of each contemporaneous time-stamped input in an ongoing manner, starting from the time of the appropriate time stamp data;

(f) assigning to each predicted value a time function/mathematical model, said time function/mathematical model being described by a time function/mathematical model comprising the general formula of:

$$EG(t)=a^N t^{N-1} e^{-at}/(N-1)!$$

wherein:
EG(t) is an elementary food component glucose activity time function;
t is an elapsed length of time measured from the time stamp of entered data;
a is the flux rate of elementary food categories; and
N is the number of compartments;

(g) improving the accuracy and precision of said mathematical model by making it an individual-specific mathematical model, by inputting user-patient anthropometrical characteristics into the time function/mathematical model;

(h) generating ongoing metabolic status predictions by combining all previous metabolite input predictions with the said individual-specific time function/mathematical model;

(i) improving the accuracy of the said individual-specific mathematical model in a recursive manner, until the said ongoing metabolic status predictions are sufficiently close to the actual measured values, said improved individual-specific model being referred to as an optimized metabolic model;

(j) contemporaneously computing usable ongoing metabolic status predictions from the optimized metabolic model and from the said input predictions in order to provide the patient with the necessary decision support information;

(k) recording and revising individual-specific medication and metabolic control parameter limits, wherein a health practitioner sets boundaries on the type of actions the patient can take and the information is stored in the said apparatus; and (l) communicating to the patient the need for proactive corrective action, wherein any such need is determined by considering steps (k) and (j).

2. The method of claim 1, wherein the contemporaneous time-stamped inputs are selected and specified in light of their predominant impact on the output value.

3. The method of claim 2, wherein the selection is made from nutrients, medication, physical activity, illness, or hormonal challenges.

4. The method of claim 3, wherein the nutrient is food, and the metabolite is "exogenous glucose" from the food.

5. The method of claim 1, wherein the metabolite output values are stored in said apparatus and are patient information.

6. The method of claim 1, whereby contemporaneous decision support in metabolic control is achieved for diabetes.

7. The method of claim 6, wherein one metabolite contemporaneous time-stamped input is exogenous insulin following an injection or infusion pump action, and said input is:

(a) generating exogenous insulin time functions using the formula:

$$I(t)=b^N t^{N-1} e^{-bt}/(N-1)!$$

wherein:
I(t) is an exogenous insulin time function;
b is the flux rate of various insulin types;
t is an elapsed length of time measured from the time stamp of entered data; and
N is the number of compartments;

(b) refining said exogenous insulin time functions by accounting for the differences in insulin bio-availability experienced by the patient depending on the injection site; and (c) refining said exogenous insulin time functions by accounting for the differences in insulin bio-availability experienced by the patient depending on the patient's degree of insulin resistance.

8. The method according to claim 6, wherein b=1.0 for regular insulin, b=0.5 for NPH insulin, b=0.25 for lente insulin, and b=0.2 ultralente insulin.

9. The method according to claim 6, wherein N=1 to 5.

10. The method according to claim 6, wherein N=4.

11. The method according to claim 6, wherein b is a population averaged value or is specific for an individual.

12. A method to estimate the ongoing dynamic bio-availability of metabolite inputs that affect metabolic control, comprising at least one of the following steps:

(a) dividing intake matter into distinct components, wherein each component is uniquely characterized by the dynamics of its transformation into a metabolite;

(b) assigning each said distinct component to an elementary category, wherein each category is described mathematically by a category-specific time function;

(c) calculating the time functions corresponding to the distinct components;

(d) calculating the combined effect of said components as a function of time;
said time function comprising a general formula of:

$$EG(t)=a^N t^{N-1} e^{-at}/(N-1)!$$

wherein:
EG(t) is an elementary food component glucose activity time function;
t is an elapsed length of time measured from the time stamp of entered data;
a is the flux rate of elementary food categories; and
N is the number of compartments.

13. The method of claim 12, wherein the elementary categories are foods, simple sugars, starches, protein, and fat, and wherein each of the said elementary categories is described by a unique pair of coefficients a and N.

14. The method of claim 13, wherein the elementary food categories are further refined by executing at least one of the following steps:

(a) dividing each food category into sub-categories, each said sub-category being described by its unique pair of coefficients a and N;

(b) dividing the food category "starches" into three subcategories corresponding to glucose-based, galactose-based, and fructose-based carbohydrates; and (c) adjusting the values of any said pair of coefficients a and N to reflect any individual-specific differences in ability to process the category or sub-category of food.

15. The method of claim 14, whereby one metabolite contemporaneous time-stamped input is exogenous glucose following a meal.

16. The method according to claim 12, wherein a=12 for all sugars, a=1/1.5 for starchy glucose, a=½ for starchy galactose, a=⅓ for starchy fructose, a=⅕ for protein, and a=⅛ for fats.

17. The method according to claim 12, wherein N=1 to 5.

18. The method according to claim 12, wherein N=4.

19. The method according to claim 12, wherein a is a population averaged value or is specific for an individual.

* * * * *

UNITED STATES PATENT AND TRADEMARK OFFICE
CERTIFICATE OF CORRECTION

PATENT NO. : 6,368,272 B1
DATED : April 9, 2002
INVENTOR(S) : Aureliu M. Porumbescu It is certified that error appears in the above-identified patent and that said Letters Patent is hereby corrected as shown below:

Column 7,
Line 20, "$EG(t)=a^N t^{N-1} e^{-at}/(N-1)$" should read -- $EG(t)=a^N t^{N-1} e^{-at}/(N-1)!$ --.
Line 30, "5, Some" should read -- 5. Some --.

Column 7, line 66 thru Column 8, line 9,
"wherein b takes specific values for each different insulin formulation; wherein "I(t)" is an exogenous insulin time function: "t" is a length of time measured from the time stump of entered data, such as the time the particular insulin was injected; "a" is the flux rate of various insulin types; and "N" is the number of compartments. In various embodiments, "b" is a population averaged value, "b" is specific for a given individual, or b=1.0 for regular insulin, b=0.5 for NPH insulin, b=0.25 for lente insulin, and b=0.2 for ultralente insulin. N can be a value from 1 to 5. Some emodiments provide for N=4."
should read
-- wherein "I(t)" is an exogenous insulin time function: "t" is a length of time measured from the time stamp of entered data, such as the time the particular insulin was injected; "a" is the flux rate of various insulin types; and "N" is the number of compartments. In various embodiments, "b" is a population averaged value, "b" is specific for a given individual, or b=1.0 for regular insulin, b=0.5 for NPH insulin, b=0.25 for lente insulin, and b=0.2 for ultralente insulin. N can be a value from 1 to 5. Some embodiments provide for N=4.
wherein b takes specific values for each different insulin formulation; --.

Column 8,
Line 2, "time stump" should read -- time stamp --.

UNITED STATES PATENT AND TRADEMARK OFFICE
CERTIFICATE OF CORRECTION

PATENT NO.   : 6,368,272 B1
DATED        : April 9, 2002
INVENTOR(S)  : Aureliu M. Porumbescu

It is certified that error appears in the above-identified patent and that said Letters Patent is hereby corrected as shown below:

Column 10,
Line 53, "device. While" should read as a new paragraph -- device. While --.
Line 59, "embodiments fall" should read -- embodiments as fall --.

Signed and Sealed this

Twelfth Day of November, 2002

*Attest:*

*Attesting Officer*

JAMES E. ROGAN
*Director of the United States Patent and Trademark Office*